(12) United States Patent
Hammad et al.

(10) Patent No.: US 11,339,109 B2
(45) Date of Patent: May 24, 2022

(54) ELECTROCHEMICAL REDUCTION OF CARBON DIOXIDE TO UPGRADE HYDROCARBON FEEDSTOCKS

(71) Applicant: Saudi Arabian Oil Company, Dhahran (SA)

(72) Inventors: Ahmad D. Hammad, Dhahran (SA); Bandar A. Fadhel, Dhahran (SA); Issam T. Amr, Dhahran (SA); Wajdi Issam Al Sadat, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/158,237

(22) Filed: Jan. 26, 2021

(65) Prior Publication Data

US 2021/0171430 A1  Jun. 10, 2021

(30) Foreign Application Priority Data

Dec. 6, 2019  (GR) .............................. 20190100550

(51) Int. Cl.
| | |
|---|---|
| *C07C 51/15* | (2006.01) |
| *C25B 1/02* | (2006.01) |
| *C25B 13/04* | (2021.01) |
| *C25B 15/02* | (2021.01) |
| *C25B 1/04* | (2021.01) |
| *C25B 3/23* | (2021.01) |
| *C25B 3/26* | (2021.01) |
| *C25B 3/25* | (2021.01) |
| *C25B 1/23* | (2021.01) |
| *C25B 3/07* | (2021.01) |
| *C25B 9/19* | (2021.01) |
| *C25B 9/73* | (2021.01) |

(52) U.S. Cl.
CPC ............... *C07C 51/15* (2013.01); *C25B 1/02* (2013.01); *C25B 1/04* (2013.01); *C25B 1/23* (2021.01); *C25B 3/07* (2021.01); *C25B 3/23* (2021.01); *C25B 3/25* (2021.01); *C25B 3/26* (2021.01); *C25B 13/04* (2013.01); *C25B 15/02* (2013.01); *C25B 9/19* (2021.01); *C25B 9/73* (2021.01)

(58) Field of Classification Search
CPC .. C07C 51/15; C25B 1/10; C25B 1/02; C25B 1/04; C25B 3/02; C25B 3/25; C25B 3/26
See application file for complete search history.

(56) References Cited

U.S. PATENT DOCUMENTS

| | | |
|---|---|---|
| 3,288,692 A | 11/1966 | Leduc |
| 3,427,235 A | 2/1969 | Leduc |

(Continued)

FOREIGN PATENT DOCUMENTS

WO    WO 2018107450    6/2018

OTHER PUBLICATIONS

Bidrawn, F et al., Efficient reduction of CO2 is a solid oxide electrolyzer, Electrochemical and Solid-state letters, vol. II, No. 9, pp. B167-B170 (Year: 2008).*

(Continued)

*Primary Examiner* — Yate' K Cutliff
(74) *Attorney, Agent, or Firm* — Fish & Richardson P.C.

(57) ABSTRACT

A system and method with a solid oxide electrolysis cell (SOEC), including feeding carbon dioxide and an olefin to the SOEC and discharging carbon monoxide and an olefin oxide from the SOEC, wherein the olefin oxide corresponds to the olefin.

20 Claims, 3 Drawing Sheets

(56) References Cited

U.S. PATENT DOCUMENTS

| | | | |
|---|---|---|---|
| 3,585,217 A | 6/1971 | Titzenthaler | |
| 3,632,497 A | 1/1972 | Leduc | |
| 3,894,059 A | 7/1975 | Selvaratnam | |
| 4,119,507 A | 10/1978 | Simmrock et al. | |
| 4,329,208 A * | 5/1982 | Vayenas | C25B 3/23 205/428 |
| 4,434,031 A | 2/1984 | Horowitz et al. | |
| 4,560,451 A | 12/1985 | Nielsen | |
| 4,602,986 A * | 7/1986 | Ellis | C25B 3/23 205/428 |
| 4,761,394 A | 8/1988 | Lauritzen | |
| 5,527,436 A | 6/1996 | Cooker et al. | |
| 6,336,791 B1 | 1/2002 | O'Toole | |
| 7,951,283 B2 * | 5/2011 | Stoots | C25B 1/04 205/637 |
| 8,075,746 B2 | 12/2011 | Hartvigsen et al. | |
| 9,115,070 B2 * | 8/2015 | Pazicky | C07C 51/09 |
| 9,175,409 B2 | 11/2015 | Sivasankar et al. | |
| 9,260,366 B2 | 2/2016 | Verhaak et al. | |
| 9,273,020 B2 * | 3/2016 | Schjodt | C07C 58/04 |
| 9,555,367 B2 | 1/2017 | Masel et al. | |
| 10,329,676 B2 | 6/2019 | Kaczur et al. | |
| 2011/0132770 A1 | 6/2011 | Sala et al. | |
| 2013/0134049 A1 | 5/2013 | Teamey et al. | |
| 2015/0057458 A1 | 2/2015 | Schjodt et al. | |
| 2017/0292197 A1 | 10/2017 | Lei et al. | |
| 2019/0032228 A1 | 1/2019 | Krause et al. | |

OTHER PUBLICATIONS

Ming, N., Modeling of solid oxide electrolysis cell for carbon dioxide electrolysis, Chemical Engineering Journal, 164, pp. 246-254 (Year: 2010).*

PCT International Search Report and Written Opinion in International Appln. No. PCT/US2020/063261, dated Feb. 17, 2021, 15 pages.

Bidrawn et al., "Efficient Reduction of CO2 in a Solid Oxide Electrolyzer," Electrochemical and Solid-State Letters, II, B167-B170, reprinted from Penn Libraries, 2008, 6 pages.

Meng et al., "Modeling of solid oxide electrolysis cell for carbon dioxide electrolysis," Chemical Engineering Journal, 164, 246-254, 2010.

* cited by examiner

ELECTROCHEMICAL REDUCTION OF CARBON DIOXIDE TO UPGRADE HYDROCARBON FEEDSTOCKS

CROSS-REFERENCE TO RELATED APPLICATIONS

This patent application is a continuation of and claims priority to U.S. patent application Ser. No. 16/786,858 filed Feb. 10, 2020, which in turn claims priority from Greek patent application number 20190100550 filed Dec. 6, 2019, the entire disclosures of which are incorporated herein by reference.

TECHNICAL FIELD

This disclosure relates to the electrochemical reduction of carbon dioxide to produce oxide anions for upgrading feedstocks.

BACKGROUND

Carbon dioxide ($CO_2$) is the primary greenhouse gas emitted through human activities. Carbon dioxide may be generated in various industrial and chemical plant facilities. At such facilities, the utilization of $CO_2$ as a feedstock may reduce $CO_2$ emissions at the facility and therefore decrease the $CO_2$ footprint of the facility. The conversion of the greenhouse gas $CO_2$ into value-added products may be beneficial.

SUMMARY

An aspect relates to a method of operating a system having a solid oxide electrolysis cell (SOEC). The method includes feeding carbon dioxide and an olefin to the SOEC, modulating the amount of the olefin fed to the SOEC, and discharging carbon monoxide and an olefin oxide from the SOEC, wherein the olefin oxide corresponds to the olefin.

Another aspect relates to a method of operating a system having an SOEC. The method includes receiving electric current at a cathode of the SOEC and electrochemically reducing carbon dioxide at the cathode via electrons of the electric current to generate carbon monoxide and oxygen ions. The method includes diffusing the oxygen ions through a solid electrolyte including a solid oxide to an anode of the SOEC and oxidizing an olefin at the anode via the oxygen ions into an olefin oxide.

Yet another aspect relates a system having an SOEC to receive carbon dioxide and an olefin and discharge carbon monoxide and an olefin oxide. The system includes a conduit to supply the olefin to the SOEC. A control valve is disposed along the conduit to modulate an amount of the olefin supplied to the SOEC. The system includes a second conduit to supply the carbon dioxide to the SOEC.

Yet another aspect relates to an SOEC system including an SOEC. The SOEC includes a cathode to electrochemically reduce carbon dioxide into carbon monoxide and oxygen ions and discharge the oxygen ions into a solid electrolyte of the SOEC. The SOEC includes an anode to receive the oxygen ions via the solid electrolyte from the cathode and oxidize an olefin with the oxygen ions into an olefin oxide corresponding to the olefin. The SOEC system includes a feed conduit to supply the carbon dioxide to a cathode side of the SOEC. The cathode side includes the cathode. The SOEC system includes a second feed conduit to supply the olefin to an anode side of the SOEC. The anode side includes the anode.

The details of one or more implementations are set forth in the accompanying drawings and the description below. Other features and advantages will be apparent from the description and drawings, and from the claims.

DETAILED DESCRIPTION

Figure 1:
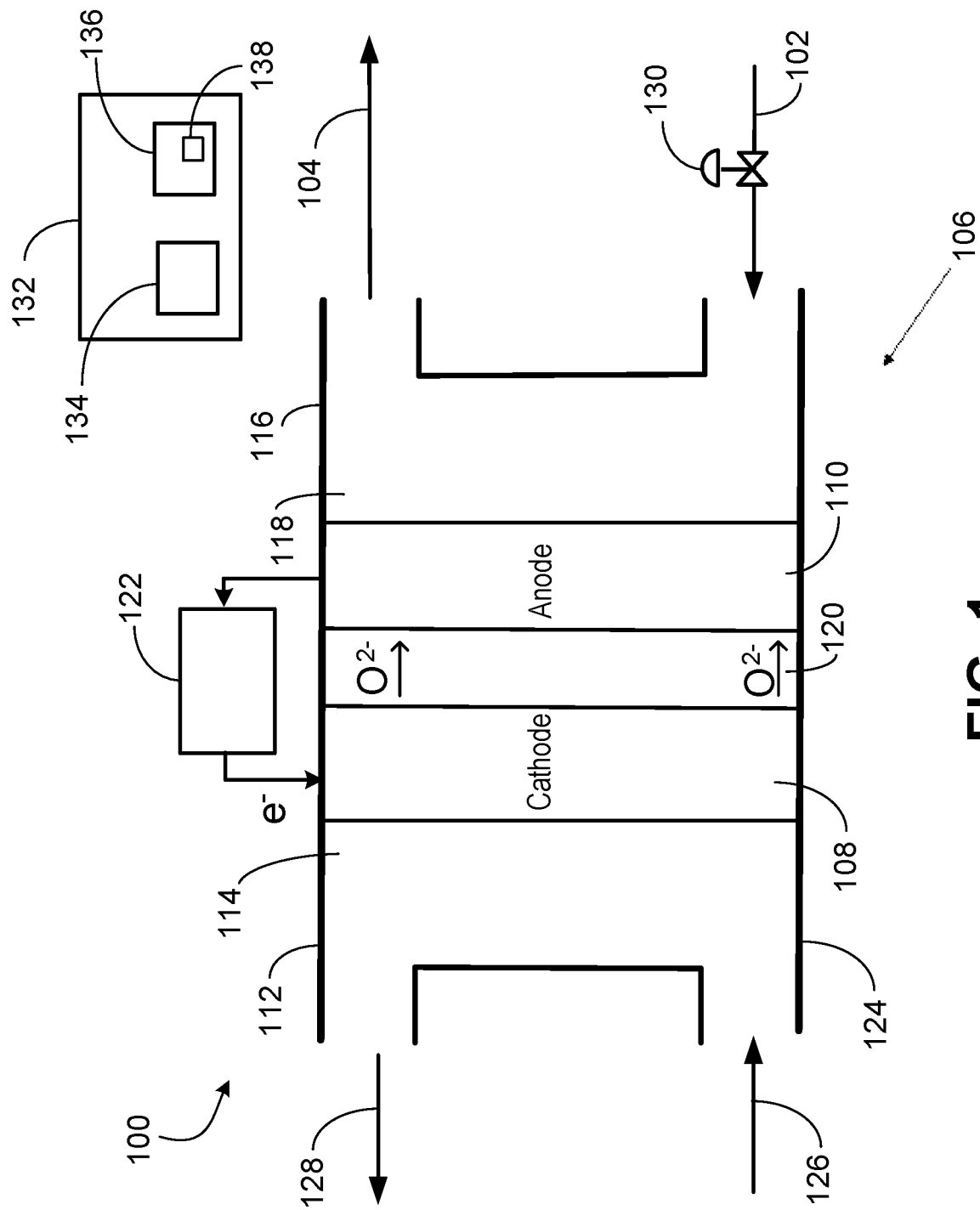
FIG. 1 is a diagram of a system having a solid oxide electrolysis cell (SOEC).

This disclosure relates to the electrochemical reduction of carbon dioxide ($CO_2$) to produce oxide anions for upgrading feedstocks including low-value feedstocks. For instance, embodiments relate to the electrochemical reduction of $CO_2$ to produce oxide anions for upgrading olefin feedstocks. Some aspects are directed to the electrochemical reduction of $CO_2$ to produce oxide anions to oxidize an olefin into an olefin oxide. The olefin oxide may be utilized as a precursor (or to generate precursors) for the production of higher value hydrocarbons. The present techniques may upgrade olefins (typically a commodity chemical) to more value-added hydrocarbon products.

As indicated, embodiments of the present techniques involve electrochemical reduction of $CO_2$. Carbon monoxide (CO) and an olefin oxide are electrocatalytically produced. The olefin oxide may be, for example, ethylene oxide, acidcyclohexene, propylene oxide, and so on. The olefin oxide may be subsequently catalytically converted into hydrocarbons (e.g., high-value hydrocarbons).

The techniques may electrochemically reduce $CO_2$ (at a cathode) to provide oxygen ions for oxidation of olefin (at the anode) into the olefin oxide. Therefore, the production of the olefin oxide involves $CO_2$. Embodiments may include electrochemically reducing $CO_2$ at the cathode to provide oxygen ions to diffuse to the anode for oxidation at the anode of the olefin into the olefin oxide.

Solid oxide electrolysis cells (SOECs) may be utilized for the electrochemical reduction of the $CO_2$ and production of the olefin oxide. On the cathode, $CO_2$ is reduced to CO and oxygen ion species ($O^{2-}$). The $O^{2-}$ is diffused via the solid electrolyte to the anode side. The solid electrolyte may be yttria-stabilized zirconia (YSZ), cerium (IV) oxide ($CeO_2$), or other materials that conduct oxygen ions. An olefin is fed to the anode side and partially oxidized by the diffused oxygen ions on the anode to form olefin oxide ($C_xH_{2x}O$). The generated CO and $C_xH_{2x}O$ may be fed to catalytic reactor(s) to produce high-value hydrocarbons, such as acrylic acid, alcohols, ethers, esters, etc.

In the desire to utilize $CO_2$ as a renewable one-carbon (C1) building block in organic synthesis, attempts have been made to synthesize ethylene oxide by reacting ethylene and $CO_2$. However, thermodynamic restrictions of such a reaction may be problematic.

While acrylic acid has been primarily produced from propylene via two stage oxidation, a benefit of ethylene oxide production is that ethylene oxide may be a precursor (or utilized to generate a precursor) for the production of acrylic acid. The reliance on ethylene to generate ethylene oxide to produce acrylic acid may reduce the production cost of acrylic acid. The reliance on ethylene instead of propylene to produce acrylic acid may reduce production cost, especially when ethylene is in abundant supply. Certain embodiments herein may convert ethylene into ethylene oxide by the electrochemical reduction of the $CO_2$. The ethylene oxide can then be utilized to produce acrylic acid or other hydrocarbon.

As discussed for present embodiments, hydrocarbons are produced through the electrochemical reduction of $CO_2$. First, the $CO_2$ and an olefin are fed to an SOEC to produce olefin oxide. Second, the produced olefin oxide may be fed to a catalytic reactor(s) to produce hydrocarbon(s) from the olefin oxide.

For the generation of an olefin oxide, gaseous $CO_2$ is fed into the cathode side of the SOEC to produce CO and $O^{2-}$ ions. These $O^{2-}$ ions diffuse through the solid electrolyte (e.g., ultra-stabilized zirconia or other material that can conduct $O^{2-}$ ions) to reach the anode side of the SOEC. An olefin ($C_xH_{2x}$) is fed to the anode side to release an electron (per olefin molecule) and form the corresponding olefin oxide ($C_xH_{2x}O$).

In certain embodiments, the $CO_2$ stream fed to the SOEC cathode side may be primarily $CO_2$, such as greater than 50 weight percent (wt %) $CO_2$, greater than 80 wt % $CO_2$, or greater than 90 wt % $CO_2$. In other embodiments, the $CO_2$ may be a component at less than 50 wt % of the stream fed to the cathode side of the SOEC.

In some embodiments, the stream fed the cathode side may include both $CO_2$ and water ($H_2O$). The $H_2O$ may also be subjected to electrochemical reduction at the SOEC cathode to generate $O^{2-}$ ions that migrate to the anode side. In particular implementations, the stream supplied to the SOEC cathode side may be a flue gas having $CO_2$ and $H_2O$, and additional compounds.

An SOEC typically has the same or similar components (e.g., cathode, anode, and electrolyte) as a solid oxide fuel cell (SOFC) but generally operates reversibly in comparison to the SOFC. An SOFC generates electricity. In contrast, an SOEC relies on an electron source (external source of electricity). The heat and electricity to operate the SOEC may be produced from renewable sources, such as solar, wind, geothermal, or hydropower. Heat may be added to the SOEC to maintain a desired operating temperature of the SOEC including the electrochemical reduction. Heat may be add to the SOEC, for example, by resistive heating (e.g., at the SOEC electrodes), a steam jacket, solar heating systems, etc. In implementations, the $CO_2$ electrolysis by the SOEC may be at a temperature in a range of 700° C. to 900° C. and at atmospheric pressure. The material of the SOEC electrodes (cathode and anode) may be based on ceramic materials that exhibit stability through reduction-oxidation (redox) cycles, electrocatalytic activity, and mixed ionic and electronic conductivity in reducing atmospheres. The material of the SOEC electrodes may be metal or metal oxides based material (e.g., Ni-based electrodes).

FIG. 1 is a system 100 to electrochemically reduce $CO_2$ to give oxygen ions to oxidize olefin 102 into olefin oxide 104. The system 100 includes an SOEC 106 having two electrodes including a cathode 108 and an anode 110. The cathode side 112 includes the cathode 108 in a cathode-side cavity 114. The anode side 116 includes the anode 110 in an anode-side cavity 118. A solid electrolyte 120 is disposed between the cathode 108 and the anode 110.

A power source 122 supplies electric current (electrons) to the cathode 108 for the electrochemical reduction of $CO_2$ into CO to occur. The power source 122 may be a battery, a power generator, an electrical grid, a renewable source of power, etc. The applied electric current may be modulated or regulated. The desired amount of current (or set point of the amount of current supplied) may be determine correlative with reaction requirements at the cathode 108 or anode 110. In implementations, the amount of current input may be based at least in part on the oxidation reaction requirement at the anode 110. The amount of current supplied by the power source 122 may be modulated variable resistor or potentiometer, or by varying voltage, and the like. The amount of current supplied by the power source 122 may be modulated via a controller directing or including the variable resistor or potentiometer, or directing the varying of the voltage, and the like.

The SOEC housing 124 may be a metal, such as stainless steel. The cathode 108 and the anode 110 may each be a ceramic or metal (or metal oxide). An example metallurgy is a nickel alloy to give nickel-based electrodes. The solid electrolyte 120 may be a solid oxide or ceramic. Examples include YSZ or $CeO_2$. Other materials that conduct oxygen ions are applicable as the solid electrolyte 120.

While only one SOEC 106 is depicted for clarity, more than one SOEC 106 may be employed. The system 100 may include an SOEC stack having multiple SOECs 106 operationally in parallel. Operating conditions for the SOEC 106 (or SOEC stack) may include an operating pressure at less than 2 atmospheres (atm), such as at about atmospheric pressure (1 atm), and an operating temperature in the range of 500° C. and 950° C. (or 700° C. to 900° C.). Operating conditions may fall outside these exemplary ranges.

In operation, $CO_2$ 126 is fed via a conduit to the cathode side 112. The cathode side 112 has an inlet to receive the $CO_2$ 126. The respective inlets and outlets of the cathode side 112 and the anode side 116 may be formed through the housing 124. In operation, the $CO_2$ is electrochemically reduced at the cathode 108 into CO via the electrons provided from the power source 122. The CO 128 discharges from an outlet of the cathode side 112 into a conduit for distribution as product or to a catalytic reactor integrated within the system 100, as discussed below. In the reduction of the $CO_2$ into CO at the cathode 108, oxygen ions ($O^{2-}$) are generated and diffuse through the solid electrolyte 120 to the anode side 116. The reaction or half reaction that takes place at the cathode side 112 may be $CO_2 + 2e^- \rightarrow CO + O^{2-}$. This reaction or half reaction (electrochemical reduction) is endothermic.

The olefin 102 is supplied via a conduit to the anode side 116. The anode side 116 has an inlet to receive the olefin 102. The olefin 102 is oxidized (into the olefin oxide 104) at the anode 110 via the oxygen ions diffused from the cathode 108. The anode 110 discharges electrons to the power source 122. The anode side 116 discharges the olefin oxide 104 through an outlet into a conduit for distribution as product or to a catalytic reactor integrated within the system 100. The reaction or half reaction that may take place at the anode side 116 is $C_xH_{2x} + O^{2-} \rightarrow C_xH_{2x}O + 2e^-$. This oxidation (or partial oxidation) reaction is generally exothermic.

The oxidation at the anode 110 may be characterized as a partial oxidation in producing olefin oxide 104 instead of $CO_2$ and water ($H_2O$). As indicated, the oxidation or partial oxidation reaction may be $C_xH_{2x}O + O^{2-} \rightarrow C_xH_{2x}O + 2e^-$. This reaction is not the result of a separate catalytic reaction but instead via the SOEC 106. SOECs with electrocatalytic anodes can be utilized for olefin partial oxidation with a specified applied potential ranging, for example, from 1 volt to 3 volts. An example of electrocatalyst for anodic partial oxidation of hydrocarbon is silver (Ag) and Ag-containing materials.

The target may be full conversion (via the partial oxidation) of the olefin 102 stream into the olefin oxide 104. In implementations where full conversion or near full conversion (e.g., 95%) is not achieved, the residual unconverted (not oxidized) olefin in the discharged olefin oxide 104 may be separated and recycled to the anode side 116.

A control valve 130 may be disposed on the conduit conveying the olefin 102 to modulate the flow rate of the olefin 102 to the anode side 116. The control valve 130 may instead be disposed on the discharge conduit conveying the olefin oxide 104. The amount of olefin 102 fed to the anode side 116 may depend, for example, on the specified production rate of the olefin oxide 104, which can be affected by the SOEC 106 production capacity of olefin oxide and other factors. The control valve 130 may be a flow control valve that controls mass rate or volumetric rate of the olefin 102 stream. The control valve 130 may be a pressure control valve that controls pressure by modulating the flow rate of the olefin 102 stream. For example, pressure may be controlled upstream or downstream of the control valve 130.

As for the $CO_2$, the amount (rate) of $CO_2$ 126 fed to the cathode side 112 may be set or modulated to generate a specified amount (rate) of oxygen ions to migrate to the anode side 116. The amount (flow rate) of $CO_2$ 126 may be modulated by a control valve (not shown) disposed on the supply conduit conveying the $CO_2$ 126 or modulated by an upstream $CO_2$ mechanical compressor, and the like. The flow rate of the $CO_2$ 126 stream, which may include additional compounds (e.g., H2O), may be modulated and controlled by the control valve. For implementations where flue gas is the $CO_2$ 126 stream, the control valve may modulate the flow rate of the flue gas fed to the cathode side 112 of the SOEC.

An adequate number of oxygen ions are generated at the cathode 108 for the oxidation on the anode side 116. For the partial oxidation on the anode 110, one oxygen ion per olefin 102 molecule is utilized. This migration of the oxygen ions from the cathode 108 to the anode 110 may be affected by the cathode 108 catalyst, ion conductivity of the solid electrolyte 120, and SOEC operating conditions such as temperature and applied electric potential by the power source. The cathode 108 catalyst may be, for example, metals, metal oxides, ceramic oxides of perovskite structure and alloys. The cathode 108 catalyst may include, for example, $Li_2MSiO_4$ (LMS), $Li_2CoSiO_4$ (LCS), $Li_2NiSiO_4$ (LNS), $LiNi_{1-x-y}Co_xMn_yO_2$, (La, Sr)$CoO_3$ (LSC) with different La—Sr ratios, $La_{1-x}Sr_xCr_{1-y}M_yO_3$ (M=Mn, Fe, Co, Ni), (La, Sr)(Fe, Co)$O_3$ (LSCF), (Sm, Sr)$CoO_3$ (SSC), and (Ba, Sr)(Co, Fe)$O_3$ (BSCF).

The system 100 may include a control system 132 having a processor 134 and memory 136 storing code 138 (e.g., instructions, logic, etc.) executed by the processor 134. The control system 132 may be or include one or more controllers. The control system 132 may direct operation of the system 100. In certain implementations, the control system 132 or controller regulates the amount of electric current provided to the cathode 108 from the power source 122. The control system 132, via calculation or user-input, may direct and specify the set point of the control valve 130 and also the control valve on the $CO_2$ supply.

The processor 134 may be one or more processors and each processor may have one or more cores. The hardware processor(s) 134 may include a microprocessor, a central processing unit (CPU), a graphic processing unit (GPU), a controller card, or other circuitry. The memory 136 may include volatile memory (for example, cache and random access memory (RAM)), nonvolatile memory (for example, hard drive, solid-state drive, and read-only memory (ROM)), and firmware. The control system 132 may include a desktop computer, laptop computer, computer server, programmable logic controller (PLC), distributed computing system (DSC), controllers, actuators, or control cards. In operation, the control system 132 may facilitate processes of the system including to direct operation of the SOEC 106. The control system 132 may receive user input or computer input that specifies the set points of control components in the system 100. The control system 132 may determine, calculate, and specify the set point of control devices. The determination can be based at least in part on the operating conditions of the system 100 including feedback information from sensors and transmitters, and the like.

In certain embodiments, the $CO_2$ 126 stream fed to the SOEC cathode side may be primarily $CO_2$, such as greater than 50 weight percent (wt %) $CO_2$, greater than 80 wt % $CO_2$, or greater than 90 wt % $CO_2$. The $CO_2$ 126 stream may be greater than 50 volume percent (vol %) $CO_2$, greater than 80 vol % $CO_2$, or greater than 90 vol % $CO_2$. In embodiments, the $CO_2$ may be a component at less than 50 wt % (or less than 50 vol %) of the $CO_2$ 126 stream fed to the cathode side of the SOEC.

In some embodiments, the $CO_2$ 126 feed may also include water ($H_2O$). The stream fed to the cathode side 112 may include both $CO_2$ and $H_2O$. In particular implementations, the $CO_2$ 126 stream supplied to the SOEC cathode side 112 may be a flue gas having the $CO_2$ and $H_2O$, and additional components.

Any $H_2O$ fed with the $CO_2$ 126 stream may also be subjected to electrochemical reduction (into $H_2$) at the SOEC cathode 108 to generate $O^{2-}$ ions. These $O^{2-}$ ions may also migrate to the anode 110 and are utilized in the oxidation of the olefin 102 at the anode 110. The produced $H_2$ may discharge in the CO 128 stream exiting from the outlet of the cathode side 112. In examples, the produced CO 128 stream having the $H_2$ may be fed to the catalytic reactor (or series of catalytic reactors) for conversion to a compound (e.g., a hydrocarbon compound).

Flue gas may be an output of a combustion and include the combustion products $CO_2$ and $H_2O$. In examples, flue gas may also be labeled as exhaust or stack gas. The composition of the flue gas may depend on the fuels or wastes combusted. Fuels combusted may include fossil-based fuels, such as natural gas or coal.

In addition to $CO_2$ and $H_2O$, components in the flue gas may include nitrogen ($N_2$), oxygen ($O_2$), carbon monoxide (CO), nitrogen oxides ($NO_x$), sulfur dioxide ($SO_2$), hydrogen sulfide ($H_2S$), and other components, as well as particulate matter. In implementations, the volume concentration of $CO_2$ in the flue gas may be, for example, less than 25% or less than 15%. The volume concentration of $H_2O$ in the flue gas may be, for example, less than 25% or less than 20%.

Figure 2:
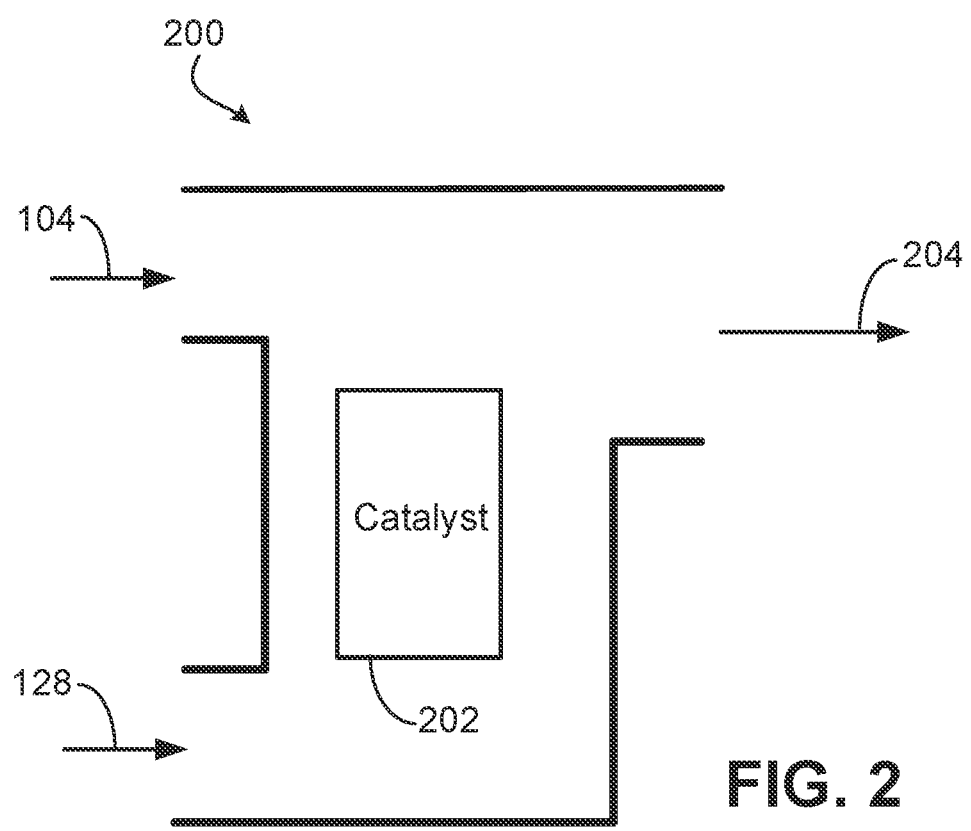
FIG. 2 is a diagram of a catalytic reactor.

As discussed below with respect to FIG. 2, the system 100 may include a catalytic reactor or series of catalytic reactors to convert the olefin oxide 104 or CO 128, or both, into a valuable hydrocarbon. The anode side 116 may discharge the olefin oxide 104 through the discharge conduit to the catalytic reactor or series of catalytic reactors (FIG. 2). The system 100 may include a motive device (e.g., compressor) disposed along the discharge conduit from the anode side 116 to provide motive force for flow of the olefin oxide 104 to the catalytic reactor.

In some implementations, the cathode side 112 may discharge the CO 128 stream (including any $H_2$) to the catalytic reactor or series of catalytic reactors. The system

100 may include a motive device (e.g., compressor) disposed along the conduit conveying the CO 128 to provide motive force for flow of the CO 128 to the catalytic reactor from the cathode side 112.

FIG. 2 is a catalytic reactor 200 that may receive from the SOEC 106 (FIG. 1) the produced olefin oxide 104 and CO 128 (and any $H_2$ along with the CO) to generate acrylic acid ($C_3H_4O_2$) or other hydrocarbon. The system 100 of FIG. 1 may incorporate the catalytic reactor 200. The catalytic reactor 200 may be a single-step or multi-step catalytic reactor. The catalytic reactor 200 may represent a series of reactors or an initial reactor in the series of reactors. The catalytic reactor 200 generally has a catalyst 202. The type of catalyst 202 may depend on the reaction(s) in the catalytic reactor 200. The catalyst 202 employed may depend on the hydrocarbon (e.g., precursor, intermediate, or product) generated in the catalytic reactor(s) 200 and that exits as hydrocarbon 204 in a discharge stream.

In operation, one or both of the olefin oxide 104 and the CO 128 may be fed to the catalytic reactor 200. The feed catalytically reacts via the catalyst 202 to give the 204, which may be produced hydrocarbon, polymer, or plastic. The product 204 may be acrylic acid, an alcohol, an ether, an ester, etc. For example, hydrolysis of the olefin oxide 104 in presence of an acid catalyst as the catalyst 202 may generate glycol as the product 204. Ethylene oxide or propylene oxide as the olefin oxide 104 may be subjected to hydrolysis to give ethylene glycol or propylene glycol, respectively, as the product 204. In other examples, polyether rubbers as the product 204 may be derived from olefin oxides 104. In yet another example, the product 204 may be bisphenol A diglycidyl ether produced from ethylene oxide as the olefin oxide 104. In other implementations, the olefin oxide 104 (e.g., ethylene oxide, propylene oxide, butylene oxide, etc.) may be reacted with ammonia to produce corresponding alkanolamines (containing a hydroxyl group) as the hydrocarbon product 204. Moreover, ethylene oxide as the olefin oxide 104 may be utilized to generate detergents or surfactants as the product 204 by ethoxylation. Additional examples are applicable.

The product 204 may be a precursor for a polymer or plastic. For instance, an epoxy may be formed from the product 204 as ethylene-oxide based precursors. The product 204 itself may be a polymer or plastic.

In some implementations of the olefin oxide 104 as ethylene oxide ($C_2H_4O$), the catalytic reactor 200 converts the ethylene oxide and the CO into a precursor that is a propiolactone ($C_3H_4O_2$) (e.g., β-propiolactone) for the production of acetic acid. In these implementations, the ethylene oxide is carbonylated with the CO in the presence of the catalyst 202 as a cobalt catalyst system [e.g., $Co(CO)_4$] to produce the precursor $C_3H_4O_2$. The carbonylation reaction may be $C_2H_4O+CO \rightarrow C_3H_4O_2$. The precursor propiolactone may discharge from the catalytic reactor 200 as the hydrocarbon 204 for distribution.

Alternatively, the precursor propiolactone may discharge from the catalytic reactor 200 to a second catalytic reactor 200 that converts the propiolactone into acrylic acid as the hydrocarbon 204 stream discharging from the second catalytic reactor 200. In one example, the catalyst 202 in this second reactor for the conversion of the β-propiolactone to acrylic acid is a phosphoric acid catalyst. Other syntheses and configurations for the conversion of the olefin oxide 104 (and CO 128) into acrylic acid are applicable.

Figure 3:
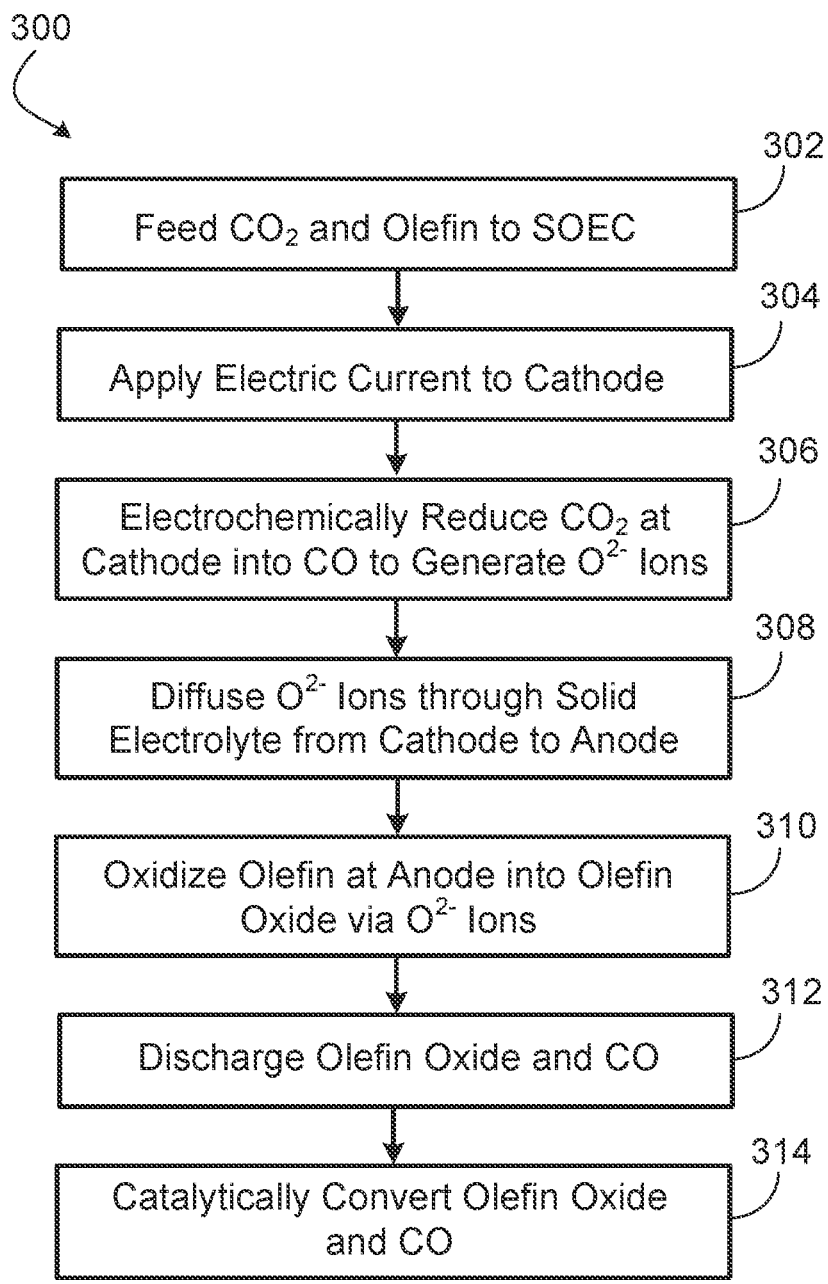
FIG. 3 is a block flow diagram of a method of operating a system having an SOEC.

FIG. 3 is a method of operating a system having an SOEC. In some implementations, the SOEC may be one SOEC of a stack of multiple SOECs arranged operationally in parallel.

At block 302, the method include supplying (feeding) $CO_2$ and olefin to the SOEC. In particular, the $CO_2$ is supplied to the cathode side of the SOEC and the olefin is supplied to the anode side of the SOEC. The method may include modulating an amount of the olefin fed to the anode side. The amount of $CO_2$ fed to the cathode side may also be controlled and altered.

The method may include supplying $H_2O$ along with the $CO_2$ to the cathode side. The method include supplying a flue gas having the $H_2O$ and the $CO_2$ to the cathode side. If flue gas is utilized, the amount of flue gas fed to the cathode side may be modulated and controlled. In examples with the presence of water in the feed with the $CO_2$ to the cathode side, the electrochemical reduction reactions at the cathode may include: (1) $CO_2+2e^- \rightarrow CO+O^{2-}$; and (2) $H_2O+2e^- \rightarrow H_2+O^{2-}$.

At block 304, the method includes applying electric current to the cathode of the SOEC. The power source that supplies the electric current may be a battery. The electric current is supplied to provide electrons to the cathode for the electrochemical reduction at the cathode. The amount of electric current applied may be modulated and adjusted.

At block 306, the method includes electrochemically reducing the $CO_2$ at the cathode into CO and generating oxygen ions via the electrochemical reduction. The electrochemical reduction relies on the electrons supplied to the cathode from the power source. The reaction or half reaction that takes place at the cathode may be $CO_2+2e^- \rightarrow CO+O^{2-}$.

The method may additionally include electrochemically reducing $H_2O$ at the cathode into $H_2$ and generating oxygen ions via the electrochemical reduction. This electrochemical reduction (if occurring) also relies on the electrons supplied to the cathode from the power source. The reaction or half reaction that takes place at the cathode may thus also include be $H_2O+2e^- \rightarrow H_2+O^{2-}$.

At block 308, the method includes diffusing the generated oxygen ions (at the cathode) through the solid electrolyte of the SOEC from the cathode to the anode. The solid electrolyte is generally a solid oxide or ceramic. This migration of the oxygen ions ($O^{2-}$) from the cathode to the anode may be affected by the cathode catalyst, ion conductivity of the solid electrolyte, and SOEC operating conditions such as temperature and applied electric potential by the power source.

At block 310, the method includes oxidizing (e.g., via partial oxidation) the olefin at the anode with the oxygen ions into an olefin oxide. The anode may discharge (release) electrons to the power source. The olefin oxide produced may generally correspond to the olefin. For instance, if the olefin is ethylene, the olefin oxide may be ethylene oxide. In another example, if the olefin is propylene, the olefin oxide generated may be propylene oxide.

At block 312, the method includes discharging the olefin oxide and the CO (and any produced $H_2$) from the SOEC. In particular, the olefin oxide is discharged from the anode side and the CO is discharged from the cathode side. Both the olefin oxide and the CO (and any produced $H_2$) may be collected for distribution as products. For CO streams having produced $H_2$, the stream having both CO and $H_2$ may be collected for distribution as a product (e.g., labeled as a syngas in some instances).

The olefin oxide and CO (and any produced $H_2$) may be discharged to a catalytic reactor or series of catalytic reactor, as discussed with respect to block 314 below. In some implementations, the catalytic reactor(s) may be integrated within the system having the SOEC.

At block 314, the method may include catalytically converting the olefin oxide and the CO (and any produced $H_2$) into a hydrocarbon having higher value than the olefin oxide. This catalytic conversion may be performed in a catalytic reactor or series of catalytic reactors. The hydrocarbon product from the conversion of the olefin oxide may be, for example, acrylic acid, an alcohol, an ether, or an ester. In the case of acrylic acid, the olefin oxide fed from the SOEC to the catalytic reactor for the conversion may be ethylene oxide. In certain implementations, the ethylene oxide may be first converted to a precursor (e.g., a propiolactone) for the acrylic acid, and then the precursor converted to acrylic acid.

An embodiment is a method of operating a system having an SOEC. The method includes feeding $CO_2$ and an olefin to the SOEC, modulating an amount of the olefin fed to the SOEC, and discharging CO and an olefin oxide from the SOEC, wherein the olefin oxide corresponds to the olefin. The method may include supplying electric current to a cathode of the SOEC and electrochemically reducing the $CO_2$ at the cathode into the CO, wherein electrochemically reducing the $CO_2$ generates oxygen ions. The method may include modulating an amount of the electric current supplied to the cathode. The method may include diffusing the oxygen ions through a solid electrolyte of the SOEC to an anode of the SOEC and oxidizing the olefin at the anode into the olefin oxide via the oxygen ions. In implementations, the method may include feeding $H_2O$ to the SOEC, electrochemically reducing the $H_2O$ at the cathode into $H_2$ (wherein electrochemically reducing the $H_2O$ generates oxygen ions), and discharging the $H_2$ from the SOEC. In these implementations, the feeding of the $CO_2$ and the feeding of the $H_2O$ (in combination or together) may involve feeding flue gas to the SOEC.

The discharging of the olefin oxide may include discharging the olefin oxide to a catalytic reactor. The method may include converting the olefin oxide via the catalytic reactor into at least one of acrylic acid, an alcohol, an ether, an ester, or a precursor for acrylic acid. In some implementations, the catalytic reactor is a series of catalytic reactors and the olefin oxide is converted into acrylic acid. The converting of the olefin oxide into acrylic acid may involve converting the olefin oxide into the precursor that is converted into acrylic acid, and wherein the olefin oxide is ethylene oxide.

Another embodiment is a method of operating a system having an SOEC. The method includes receiving electric current at a cathode of the SOEC and electrochemically reducing $CO_2$ at the cathode via electrons of the electric current to generate CO and oxygen ions. The method includes diffusing the oxygen ions through a solid electrolyte (including a solid oxide) to an anode of the SOEC and oxidizing an olefin at the anode via the oxygen ions into an olefin oxide. The method may include modulating an amount of the electric current received at the cathode. In certain implementations, the method may include electrochemically reducing $H_2O$ at the cathode via electrons of the electric current to generate hydrogen and oxygen ions. The method may include providing a flue gas having the $CO_2$ and the $H_2O$ to a cathode side of the SOEC. The method may include modulating the amount of olefin received at the anode. In some implementations, the method may include discharging the olefin oxide from an anode side of the SOEC to a catalytic reactor and converting the olefin oxide via the catalytic reactor into a compound including a hydrocarbon. The catalytic reactor may be a series of catalytic reactors. The catalytic reactor may be a first reactor in series of catalytic reactors. In particular implementations, the olefin fed to the SOEC is ethylene and the produced olefin oxide is ethylene oxide that is converted into the hydrocarbon being acrylic acid.

Yet another embodiment is a system having an SOEC to receive $CO_2$ and an olefin and discharge CO and an olefin oxide. The system includes a conduit to supply the olefin to the SOEC. A control valve is disposed along the conduit to modulate an amount of the olefin supplied to the SOEC. The system may include a controller to direct a set point of the control valve. The system includes a second conduit to supply the $CO_2$ to the SOEC. The SOEC may include: (1) a cathode to electrochemically reduce the $CO_2$ and generate oxygen ions and the CO, wherein the cathode is coupled to a power source to supply electric current to the cathode; (2) a solid electrolyte to diffuse the oxygen ions from the cathode to an anode, wherein the solid electrolyte includes a solid oxide; and (3) the anode to oxidize, via the oxygen ions, the olefin into the olefin oxide. The system may include a controller to modulate an amount of the electric current supplied to the cathode, wherein the cathode electrochemically reduces the $CO_2$ to the CO via the electric current. The system may include the power source (e.g., a battery) to supply the electric current to the cathode. The system may include a catalytic reactor to convert the olefin oxide into a hydrocarbon different than the olefin oxide, wherein the catalytic reactor has an inlet to receive the olefin oxide.

Yet another embodiment is an SOEC system having an SOEC. The SOEC includes a cathode to electrochemically reduce carbon dioxide into carbon monoxide and oxygen ions and discharge the oxygen ions into a solid electrolyte of the SOEC. The SOEC includes an anode to receive the oxygen ions via the solid electrolyte from the cathode and oxidize an olefin with the oxygen ions into an olefin oxide corresponding to the olefin. The SOEC system includes a feed conduit to supply the carbon dioxide to a cathode side of the SOEC. The cathode side includes the cathode. In some implementations, the feed conduit to supply a flue gas having the carbon dioxide and also water to the cathode side. The SOEC system includes a second feed conduit to supply the olefin to an anode side of the SOEC. The anode side includes the anode. In implementations, the SOEC system may include a control valve disposed along the second feed conduit to modulate the amount of the olefin supplied to the cathode side. The SOEC system may be coupled to or include a power source to supply electric current to the cathode. The power source may be, for example, a battery, a power generator, or an electrical grid, or any combinations thereof. The SOEC system may include a controller to modulate the amount of the electric current receive at (or supplied to) the cathode. The SOEC may include a conduit to discharge the olefin oxide to a catalytic reactor. The SOEC may include a second conduit to discharge the carbon monoxide to the catalytic reactor.

A number of implementations have been described. Nevertheless, it will be understood that various modifications may be made without departing from the spirit and scope of the disclosure.

What is claimed is:
1. A method of operating a system having a solid oxide electrolysis cell (SOEC), comprising:
feeding carbon dioxide and an olefin to the SOEC;

electrochemically reducing the carbon dioxide at a cathode of the SOEC into carbon monoxide, wherein electrochemically reducing the carbon dioxide generates oxygen ions;

diffusing the oxygen ions through a solid electrolyte of the SOEC to an anode of the SOEC; and oxidizing the olefin at the anode into an olefin oxide via the oxygen ions at an operating temperature in a range of 500° C. to 950° C., wherein the olefin oxide corresponds to the olefin.

2. The method of claim 1, comprising discharging carbon monoxide from the SOEC, wherein the operating temperature is in a range of 700° C. to 900° C.

3. The method of claim 1, comprising modulating an amount of the olefin fed to the SOEC.

4. The method of claim 1, comprising supplying electric current to the cathode.

5. The method of claim 4, comprising modulating an amount of the electric current supplied to the cathode.

6. The method of claim 1, comprising:

feeding water ($H_2O$) to the SOEC;

electrochemically reducing the water at the cathode into hydrogen ($H_2$), wherein electrochemically reducing the water generates oxygen ions; and discharging the hydrogen from the SOEC.

7. The method of claim 1, comprising discharging the olefin oxide from the SOEC, wherein an adequate number of oxygen ions are generated at the cathode for oxidizing the olefin fed to the SOEC, wherein oxidizing the olefin at the anode comprises utilizing one oxygen ion of the oxygen ions generated at the cathode per olefin molecule of the olefin fed to the SOEC and converted into the olefin oxide discharged from the SOEC.

8. The method of claim 7, comprising:

discharging the olefin oxide from the SOEC; and converting the olefin oxide via a catalytic reactor into at least one of acrylic acid, an alcohol, an ether, or an ester, wherein discharging the olefin oxide from the SOEC comprises discharging the olefin oxide to the catalytic reactor.

9. The method of claim 8, wherein the catalytic reactor comprises a series of catalytic reactors, and wherein the olefin oxide is converted into acrylic acid.

10. The method of claim 9, and wherein converting the olefin oxide comprises converting the olefin oxide via the catalytic reactor into the acrylic acid, and wherein the olefin oxide comprises ethylene oxide.

11. A method of operating a system having a solid oxide electrolysis cell (SOEC), comprising:

receiving electric current at a cathode of the SOEC;

electrochemically reducing carbon dioxide at the cathode via electrons of the electric current to generate carbon monoxide and oxygen ions;

diffusing the oxygen ions through a solid electrolyte comprising a solid oxide to an anode of the SOEC; and oxidizing an olefin at the anode via the oxygen ions into an olefin oxide at an operating temperature in a range of 500° C. to 950° C.

12. The method of claim 11, comprising providing the carbon dioxide and the olefin to the SOEC, wherein the operating temperature of the SOEC is in a range of 700° C. to 900° C., and wherein oxidizing the olefin at the anode into the olefin oxide comprises utilizing one oxygen ion of the oxygen ions generated at the cathode per olefin molecule of the olefin provided to the SOEC.

13. The method of claim 12, wherein providing the carbon dioxide to the SOEC comprises providing the carbon dioxide to a cathode side of the SOEC.

14. The method of claim 12, wherein providing the olefin to the SOEC comprises providing the olefin to an anode side of the SOEC.

15. The method of claim 12, comprising modulating an amount of the olefin provided to the SOEC.

16. The method of claim 11, comprising electrochemically reducing water at the cathode via electrons of the electric current to generate hydrogen and oxygen ions.

17. The method of claim 11, comprising discharging the olefin oxide from an anode side of the SOEC to a catalytic reactor and converting the olefin oxide via the catalytic reactor into acrylic acid.

18. The method of claim 17, wherein the olefin comprises ethylene, and wherein the olefin oxide comprises ethylene oxide.

19. The method of claim 17, wherein the catalytic reactor comprises a first reactor in a series of catalytic reactors.

20. The method of claim 17, wherein the catalytic reactor comprises a series of catalytic reactors.

* * * * *

UNITED STATES PATENT AND TRADEMARK OFFICE
CERTIFICATE OF CORRECTION

| | |
|---|---|
| PATENT NO. | : 11,339,109 B2 |
| APPLICATION NO. | : 17/158237 |
| DATED | : May 24, 2022 |
| INVENTOR(S) | : Hammad et al. |

It is certified that error appears in the above-identified patent and that said Letters Patent is hereby corrected as shown below:

On the Title Page

Column 1, before (30) Foreign Application Priority Data, please insert:
-- Related U.S. Application Data
(63) Continuation of application No. 16/786,858, filed on Feb. 10, 2020, now Pat. No. 11,001,549. --

Signed and Sealed this
Twelfth Day of July, 2022

Katherine Kelly Vidal
*Director of the United States Patent and Trademark Office*